(12) United States Patent
Stamatas et al.

(10) Patent No.: US 8,182,425 B2
(45) Date of Patent: May 22, 2012

(54) METHOD FOR MEASURING SKIN HYDRATION

(75) Inventors: Georgios N. Stamatas, Issy-les Moulineaux (FR); Michael Cobb, Paris (FR); Christiane Bertin, Clamart (FR)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 92 days.

(21) Appl. No.: 12/782,281

(22) Filed: May 18, 2010

(65) Prior Publication Data
US 2011/0288385 A1    Nov. 24, 2011

(51) Int. Cl.
*A61B 5/00*    (2006.01)
(52) U.S. Cl. .................. 600/306; 600/307; 600/473
(58) Field of Classification Search .......... 600/306–307, 600/473–476
See application file for complete search history.

(56) References Cited

U.S. PATENT DOCUMENTS

| | | | | |
|---|---|---|---|---|
| 5,836,872 | A * | 11/1998 | Kenet et al. ............... | 600/306 |
| 2002/0065468 | A1* | 5/2002 | Utzinger et al. .......... | 600/476 |
| 2006/0239547 | A1 | 10/2006 | Robinson et al. | |
| 2007/0167835 | A1* | 7/2007 | Yu et al. .................... | 600/476 |
| 2010/0210931 | A1* | 8/2010 | Cuccia et al. ............. | 600/328 |

OTHER PUBLICATIONS

Arimoto et al, "Estimation of Water Content Distribution in the Skin Using Dualband Polarization Imaging", Skin Research and Technology, vol. 13, pp. 49-54 (2007).
Attas et al, "Long-wavelength near-infrared spectroscopic imaging for in-vivo skin hydration measurements", Vibrational Spectroscopy, vol. 28, pp. 37-43 (2002).
Stamatas et al., "In Vivo Documentation of Cutaneous Inflammation Using Spectral Imaging", Journal of Biomedical Optics, vol. 12(5), pp. 051603-1-051603-7(2007).

* cited by examiner

*Primary Examiner* — Patricia Mallari
*Assistant Examiner* — Michael D'Angelo

(57) ABSTRACT

The methods of this invention relate to means for measuring skin hydration. The methods of this invention utilize at least two wavelengths filtered by at least two polarizers to create digital images of skin treated with personal care products. The methods are useful for demonstrating the efficacy of skin care products intended to increase skin hydration and/or protect the skin from dehydration, even when such dehydration is not apparent to the naked eye.

6 Claims, 8 Drawing Sheets

//]::

METHOD FOR MEASURING SKIN HYDRATION

BACKGROUND OF THE INVENTION

This invention relates to a method for measuring skin hydration. The method of this invention utilizes at least two wavelengths filtered by at least two polarizers to create digital images of skin treated with personal care products. This method is useful for demonstrating the efficacy of skin care products intended to increase skin hydration and/or protect the skin from dehydration, even when such dehydration is not apparent to the naked eye.

FIELD OF THE INVENTION

The term "skin hydration" refers to the amount of water in the stratum corneum, the outermost horny layer of the skin, and is often used as one of the measurements of skin health. General characteristics of healthy skin include a gradual increase in the water concentration of the stratum corneum from approximately 15 to 25% at the skin surface to around 70% in the viable epidermis. Dehydrated skin is often associated with poor barrier function, often resulting in reduced protection against disease causing organisms, toxins, and the environment. One way to increase hydration is to apply moisturizers to the skin.

Skin hydration is typically measured by either electrical (e.g., measuring skin capacitance, conductance, impedance) or optical (e.g., imaging, spectroscopy) techniques. Electrical methods are the most common and measure the stratum corneum water content indirectly with a probe. The measurement point is where the probe contacts the skin surface. Electrical measurement probes are typically based on capacitance (e.g., Corneometer® CM420 by Courage+Khazaka electronic GmbH, Cologne, Germany), conductance (e.g., Skicon-200EX®, IBS-Hamamatsu Co., Japan) and impedance (e.g., Nova DPM 900, NOVA Technology Corp., Portsmouth, N.H., USA).

New optical methods utilizing digital imaging have been described in recent publications.

Attas et al. in Vibrational Spectroscopy v. 28 (2002) pp 37-43 utilizes the NIR (near infrared) region of the electromagnetic spectrum. Attas discusses a single wavelength (1460 nm), a ratio between the maximum and minimum water absorption in the IR region and integrating the region from 1300-1600 nm. As this approach operates in the IR region, beyond 1000 nm, it requires specialized and expensive equipment. In addition, Attas does not describe the use of parallel or cross-parallel polarizing filters.

Arimoto, in Skin Research and Technology v. 13 (2007) pp. 49-54, describes the combination of cross- and parallel-polarization in the visible region to enhance skin surface information. While the method of Arimoto provides an indirect distribution of the skin's water content, it does not provide a quantifiable water map or take into account the contribution of melanin at 500 nm.

Robinson et al. (US 20060239547A1) sets forth methods and apparati for determining cosmetic skin properties from optical measurements of the skin. Robinson does not generate digital images, which allows for mapping of the skin surface.

Stamatas et al., in Journal of Biomedical Optics v. 12(5) (2007) pp. 051603-1 to 051603-7, discuss a spectral imaging approach appropriate for studying water deeper in the skin by using only the cross-polarized light.

SUMMARY OF THE INVENTION

The methods of this invention relate to a digital imaging method for measuring skin hydration that provides a quantifiable visual map of skin surface hydration using polarized light at different spectral wavelengths: one wavelength that exhibits strong absorption of electromagnetic radiation by water and another wavelength that exhibits minimal absorption of electromagnetic radiation by water. Cross-polarized and parallel-polarized digital images are generated at the first wavelength. The combination of cross- and parallel-polarized images obtained at the first wavelength are then normalized to that of the second wavelength, thereby generating a visual map that provides water content information of the skin.

The methods of this invention provide a more direct method of measuring skin hydration than previously-known methods because it is based on the absorption properties of water. The result is a digital image (map) that can be used to visualize and quantify the amount of water contained within the various layers of skin, including the stratum corneum.

DETAILED DESCRIPTION OF PREFERRED EMBODIMENTS

Figure 1:
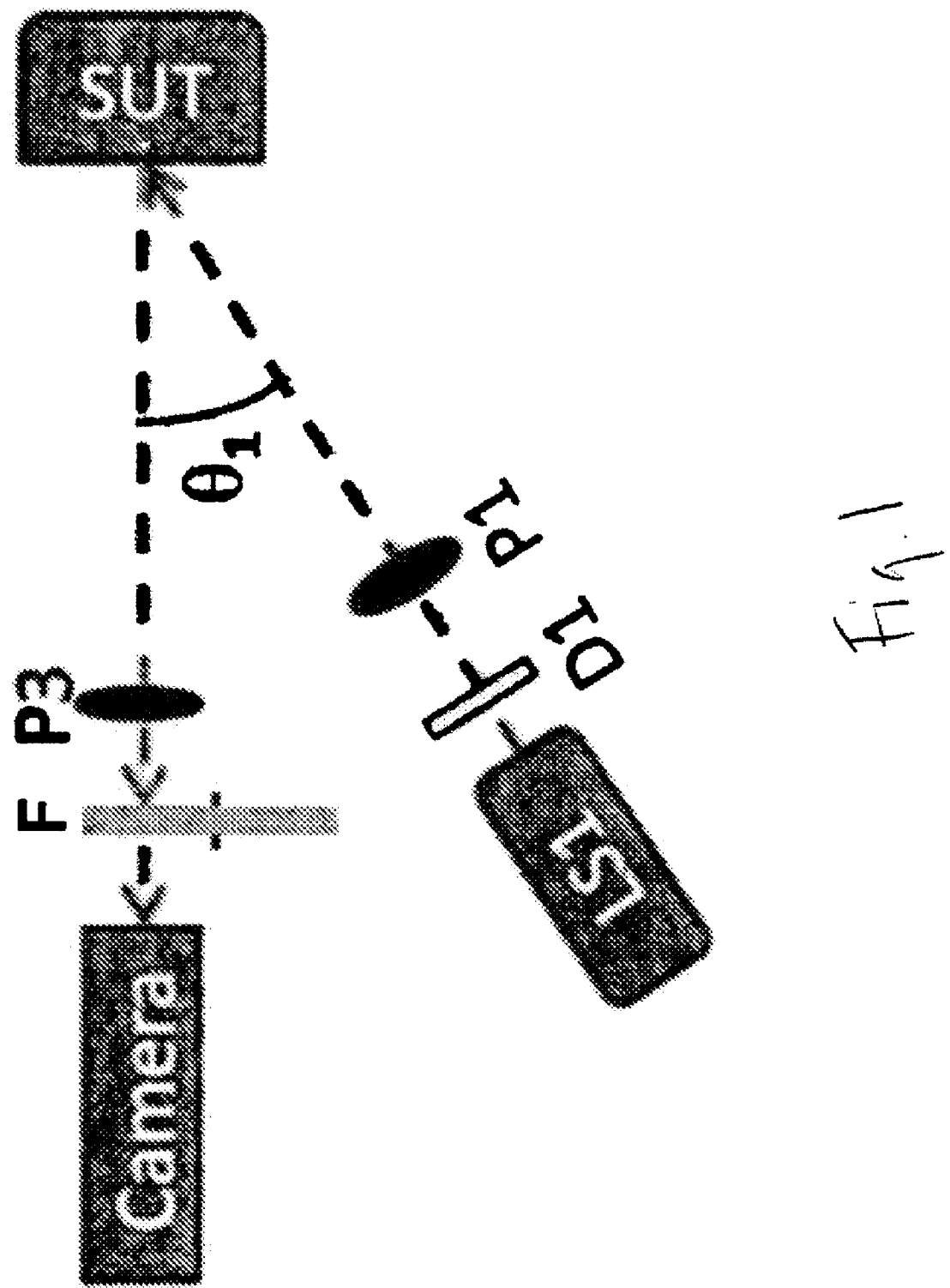
FIG. 1 is a schematic diagram showing an example apparatus suitable for measuring skin hydration according to the present invention.

The present invention utilizes a spectral imaging system to generate images of the skin. One suitable spectral imaging system includes a custom-made camera (FORTH Photonics, Athens, Greece) with a 25 mm macro lens and a linear polarizing filter capable of multispectral (up to about 30 narrow band filters) and/or hyperspectral (greater than about 30 narrow band filters) imaging (hereafter, both multispectral and hyperspectral are collectively "ms/hs"). The camera contains multiple narrow band filters, for example from 4 to 50 narrow band filters in the spectral range of about 700 to about 1000 nm. The settings for the image acquisition including filter selection, exposure time, and camera gain are preferably controlled through computer software.

In another embodiment, a commercial camera (e.g., Nikon G10) is used with a filter wheel in front of the camera. The filter wheel can be preferably computer controlled utilizing the appropriate software or commands to select a desired filter and then subsequently change the filter wheel position to the desired filter (e.g., moving the filter from 800 nm to 970 nm).

A linearly polarized broadband light source is preferably utilized in the methods of this invention. One suitable linearly polarized light source is the v600, Syris, Gray, Me.

The following terms used herein have the meanings ascribed to them below:

"ORTHOGONAL OR CROSS POLARIZATION CONDITIONS": means imaging conditions that include a first polarizer filter in front of the light source and a second polarizer filter in front of the camera lens with the two filters having their polarization axes orthogonal to each other.

"PARALLEL POLARIZATION CONDITIONS": imaging conditions that include a first polarizer filter in front of the light source and a second polarizer filter in front of the camera lens with the two filters having their polarization axes parallel to each other.

In one embodiment, the methods of this invention include the step of taking a polarized photograph of the subject. What is meant by "polarized photograph" is a photograph of the subject taken (i) with a light source that emits light through a polarizing filter and/or (ii) through a polarized filter that filters light prior to entering the camera's lens.

As used herein, the identifier "PP" shall mean parallel polarized.

As used herein, the identifier "XP" shall mean cross-polarized or orthogonal.

In one embodiment, the camera and one or more light sources, preferably one, are on about the same plane as the subject's skin to be photographed, and the light sources are placed so that the angle formed by each light source(s), subject's skin, and camera is about 15 to about 70 degrees, more preferably, about 45 degrees. In one embodiment, a polarizing filter is placed in front of each light source.

What is meant by a "polarizing filter" is a filter that filters incoming light to emit polarized light. Examples of polarizing filters include, but are not limited to, polarizing plates such as those available from Edmund Scientific (Barrington, N.J. USA), polarizing prisms such as Glan Thomson polarizing prisms, or a polarizing reflector that reflects light at about the Brewster angle. Polarizing filters may be linear or circular polarizing filters.

Measurements are preferably performed at two wavelengths. The first wavelength, $\lambda_1$, is preferably in the range from about 700 to about 900 nm, more preferably 800 nm, a range in which water does not exhibit strong light absorption. The second wavelength, $\lambda_2$, is preferably in the range from about 900 to about 1000 nm, preferably 970 nm, a range in which light absorbance by water is high.

"SPECULAR REFLECTION" or "GLARE" is the part of the light that changes direction upon incidence on a surface of a material with a different index of refraction than the medium from which the light emanates. In the case of skin imaging the first medium is air and the second is the stratum corneum. In this case, specular reflection is about 4% of the incident light intensity (based on Fresnel's law). The rest of the incident light penetrates the skin tissue and undergoes absorption. The light in the skin tissue will either exit the skin after a few scattering events in the stratum corneum (thereby maintaining its polarization state) or penetrate deeper and undergo multiple reflection events before exiting the skin as diffuse reflected light.

In one example of the methods of this invention (and as shown in FIG. 1), a halogen light source LS1 emits light that goes through polarizer P1 before arriving to the skin surface. The light reflected from the skin then goes through a second polarizer P3. P1 and P3 are two different polarizers such that one may be oriented orthogonal or parallel to the other. For example, if P1 is set in a particular plane, then P3 may be rotated such that it is orthogonal or parallel to P1. As shown in FIG. 1, diffuser D1 may be used in order to obtain more uniform illumination. However, the diffuser D1 as shown in the embodiment of FIG. 1, is not necessary to the methods of this invention.

Figure 2:
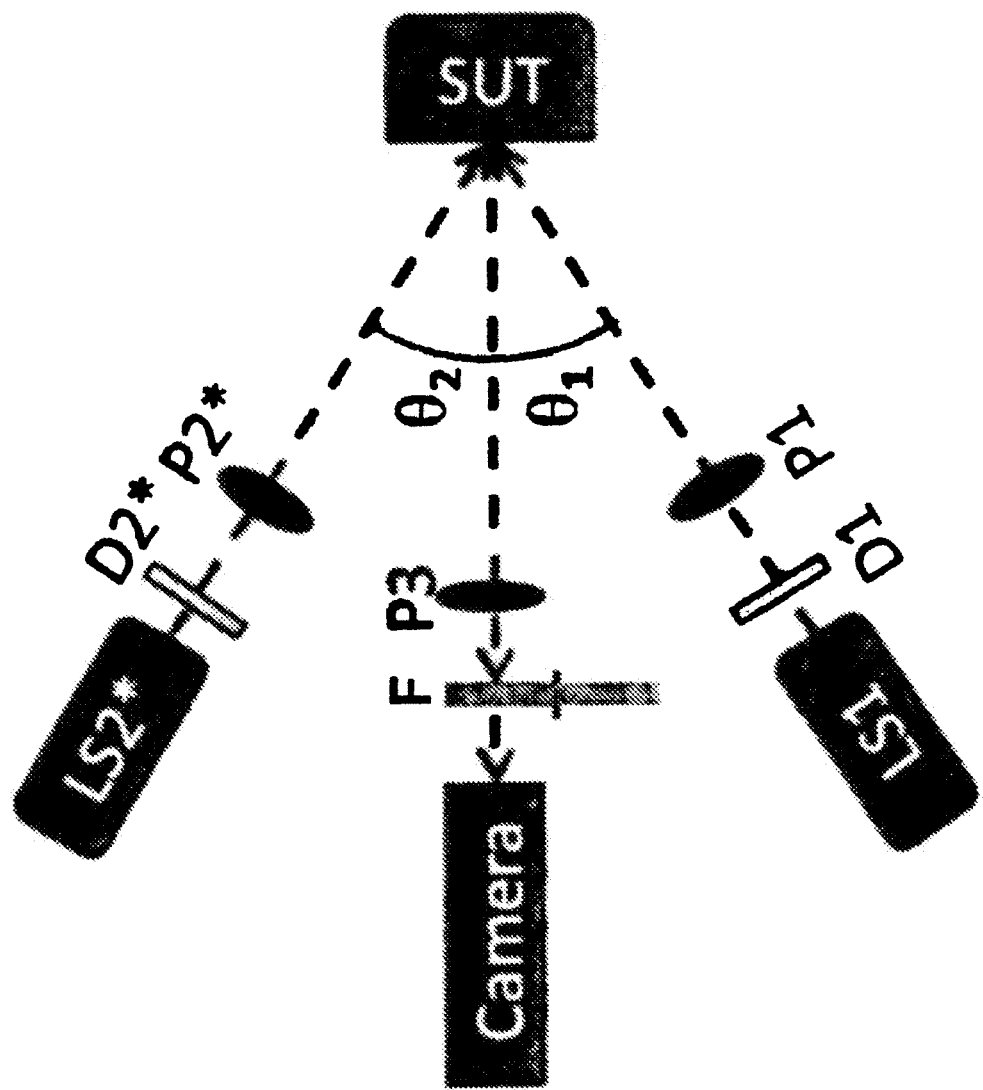
FIG. 2 is a schematic diagram showing an alternate example apparatus suitable for measuring skin hydration according to the present invention.

The light from LS1 goes through P1 targeting a specific skin area SUT. This light is then reflected off the target skin at a specific angle ($\theta_1$), travels through the second polarizer (shown as P3 in FIG. 1) and filter wheel F to be captured by a digital camera. Filter wheel F1 is capable of switching between band pass filters with bands centered at different wavelengths. Preferably the band pass filters are narrow band (with bandwidth of 5-20 nm) filters. Preferably the filters are of high transmission (>80%). Preferably the filters are interference (or dichroic) filters. In one embodiment the filter wheel may be replaced by a liquid crystal tunable filter (LCTF) system. For the present invention, the preferred wavelengths are from about 700 to about 900 nm, more preferably 800 nm and from about 900 to about 1000 nm, more preferably 970 nm. To analyze the skin surface, four images are captured or taken by the digital camera:

1. a digital image of skin under parallel polarization conditions filtered at a first wavelength $\lambda_1$ of from about 700 to about 900 nm;
2. a digital image of skin under orthogonal (cross) polarization conditions filtered at a first wavelength $\lambda_1$ of from about 700 to about 900 nm;
3. a digital image of skin under parallel polarization conditions filtered at a second wavelength $\lambda_2$ of from about 900 to about 1000 nm;
4. a digital image of skin under orthogonal (cross) polarization conditions filtered at a second wavelength $\lambda_2$ of from about 900 to about 1000 nm;

In another example of the present invention shown in FIG. 2, two halogen light sources (LS1 and LS2) are shown in combination with optional diffusers (D1 and D2) and polarizers (P1 and P2, respectively). In a preferred embodiment, P1 and P2 are oriented in the same manner. A third polarizer (shown as P3 in FIG. 2) is oriented orthogonal or parallel to P1 and P2.

In FIG. 2, the light from LS1 and LS2 is aligned through P1 and P2 to a specific skin area. This light is then reflected from the target skin, passed through P3 and a filter wheel and then captured by a digital camera. In the example shown in FIG. 2, the angles of reflectance $\theta_1$ and $\theta_2$ are preferably the same.

The recorded images are put into an equation. The equation is applied on a pixel by pixel basis, which results in a reflectance value (number). The numbers are then used to create a map of the skin surface. This map correlates to the hydration of the skin.

"REFLECTANCE VALUES": the light intensity being recorded by the camera at a particular wavelength and a particular polarization state (orthogonal or parallel).

The orthogonal polarized image and the parallel polarized image obtained at two wavelengths is preferably used to determine light absorption due to water, as defined by the following equation:

$$-\log \frac{(\text{reflectance at } \lambda_{2PP} - \alpha \text{ reflectance at } \lambda_{2XP})}{(\text{reflectance at } \lambda_{1PP} - \alpha \text{ reflectance at } \lambda_{1XP})}$$

As used herein, the term "α" is a term that is adjusted to account for the amount of diffused reflected light in the parallel polarized image. In a preferred embodiment of the invention, α is preferably between 0 and 1, more preferably between about 0.2 and about 0.4, preferably about 0.3.

As used herein, "λ" shall mean wavelength measured in nanometers or nm at which the reflected light is filtered before entering the camera detector.

In another embodiment of the method of this invention, a light diffuser is placed between the light source unit and the polarizing filter.

In yet another embodiment of the method of this invention, a linear polarizing filter is used at the light source and the linear polarizing filter is arranged such that the electric field of the emitted light is about parallel or perpendicular (orthogonal) to the plane formed by the light source, the person's skin, and the camera.

In another embodiment of the method of this invention, the polarized light source(s) are positioned on a vertical plane above the camera and the subject's skin so that the angle formed by the light source, subject's skin and camera is about 15 to 70 degrees, preferably about 45 degrees. The light source(s) are filtered with a linear polarizing filter that is placed with the transmitted electric field in the vertical direction (e.g., parallel to the plane).

Example of Crossed- and Parallel-Polarized Images Taken at 800 and 970 nm

Figure 3:
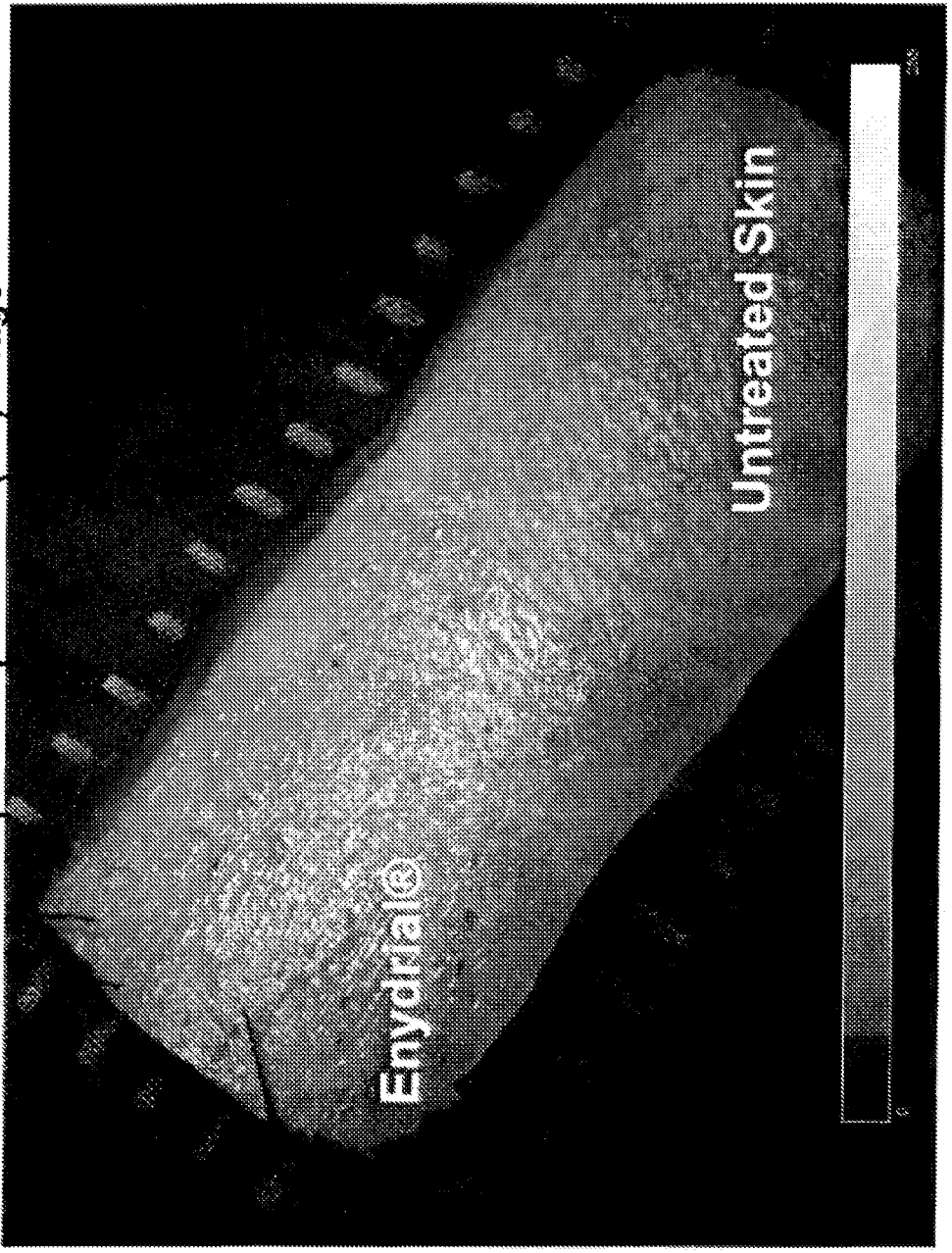
FIG. 3 shows the image taken of a subject undergoing treatment at 800 nm under parallel polarization conditions.
Figure 4:
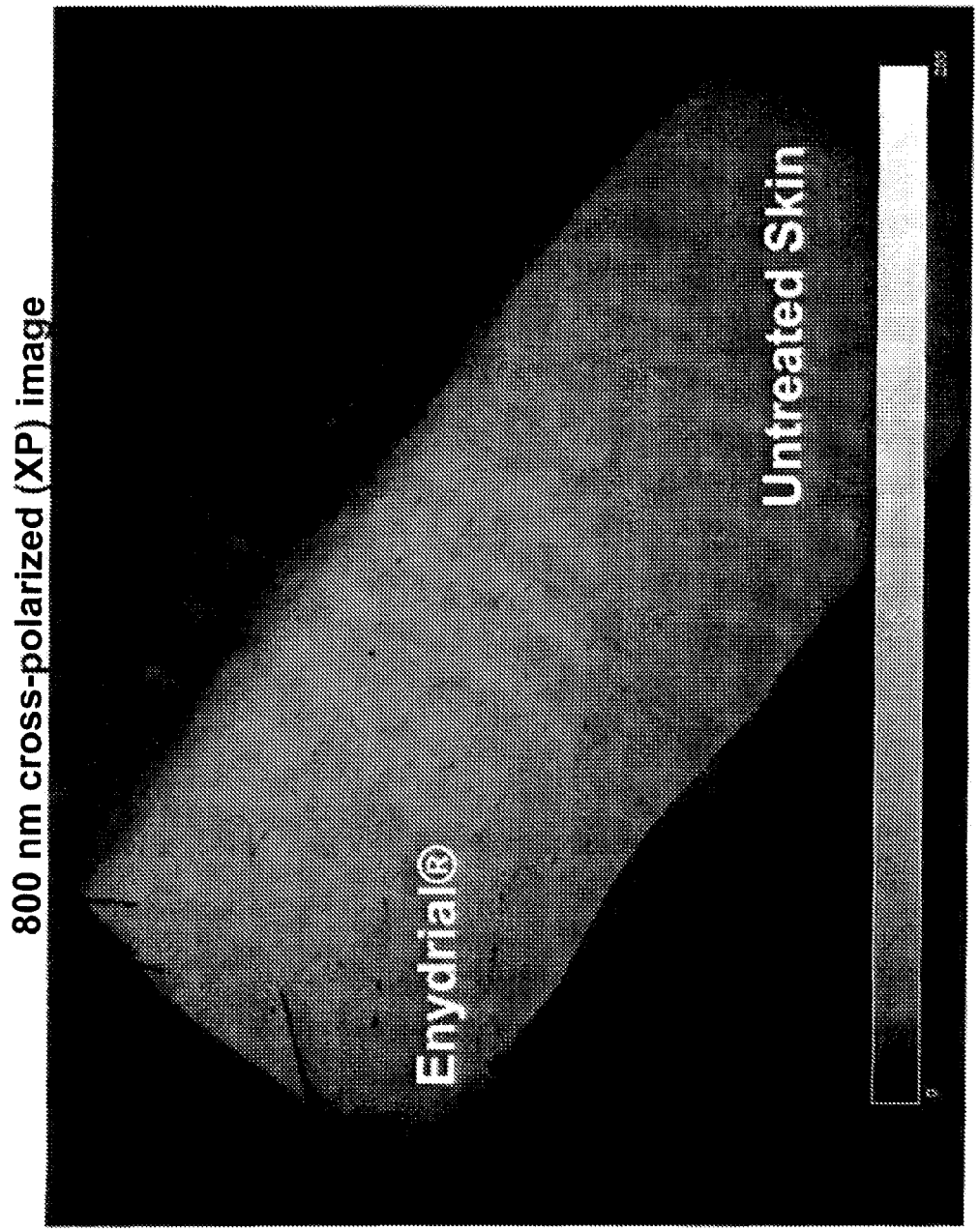
FIG. 4 shows the image taken of a subject undergoing treatment at 800 nm under cross-polarization conditions.
Figure 5:
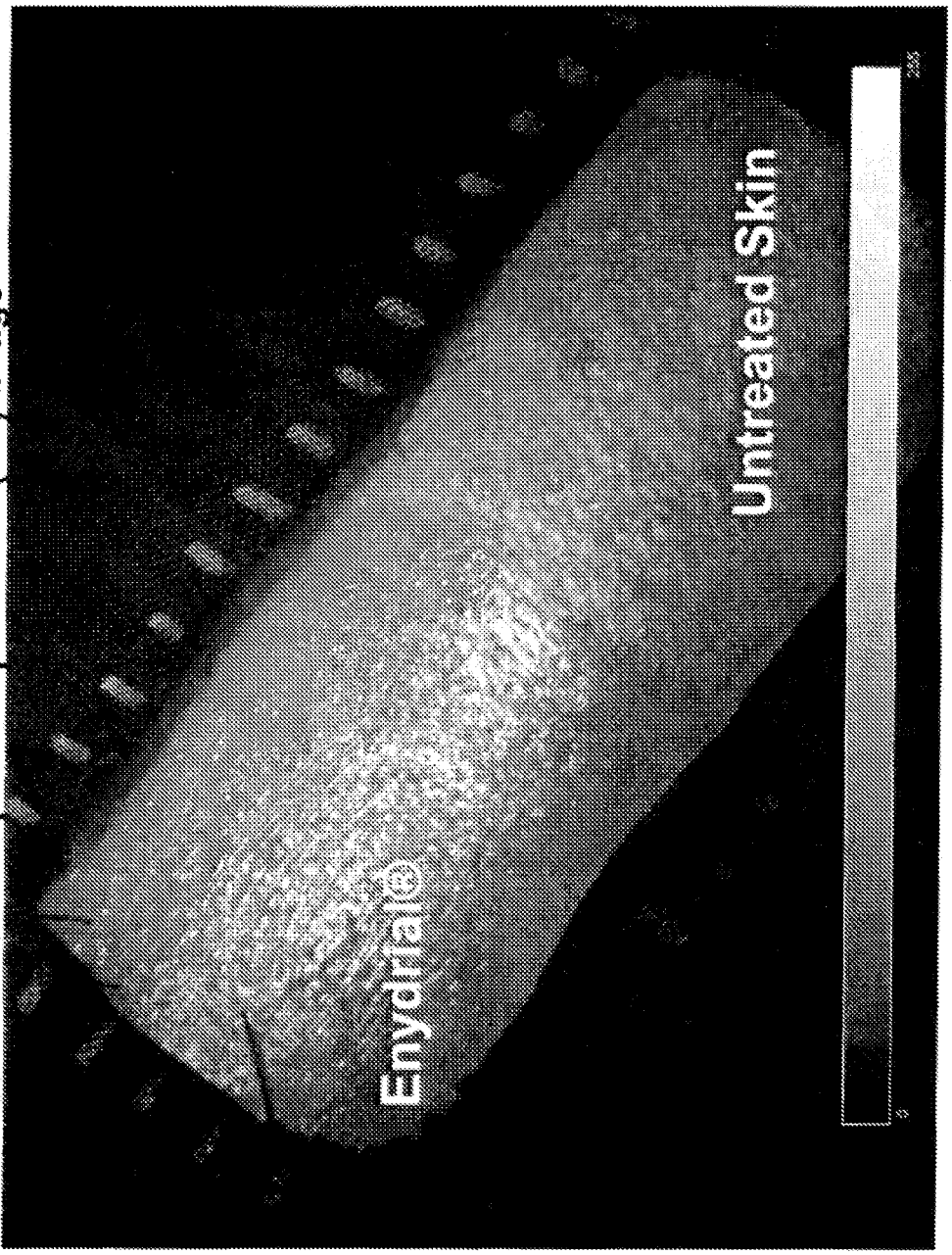
FIG. 5 shows the image taken of a subject undergoing treatment at 970 nm under parallel polarization conditions.
Figure 6:
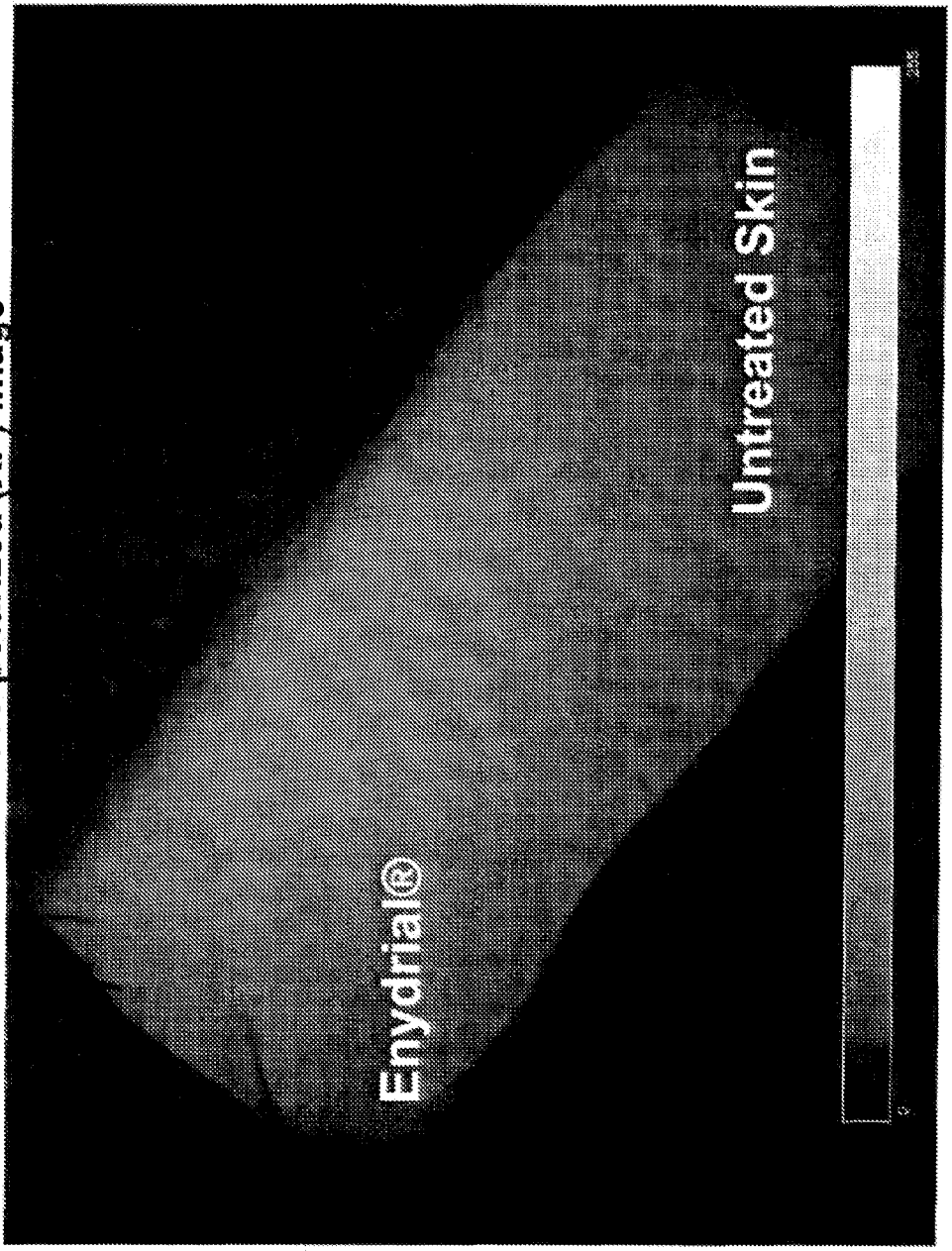
FIG. 6 shows the image taken of a subject undergoing treatment at 970 nm under cross-polarization conditions.

The imaging system was set up in the configuration shown in FIG. 1. The optional diffuser D1 was not used to acquire these images. The angle $\theta_1$ was approximately 25 degrees. Using the skin area from the lower left leg of a 28 year old male volunteer exhibiting dry skin, a hydration cream, about 0.1 ml of Enydrial® Lait Hydratant Corps (available from RoC, France) was applied evenly to a specified area of the lower leg with bare fingers. Any excess cream was removed by blotting the surface with a paper towel. The application time took approximately one minute and the measurements were taken within about five minutes after application. Four images were taken. The first image (FIG. 3) was taken at 800 nm under parallel polarization conditions. The second image (FIG. 4) was taken at 800 nm under cross-polarization conditions. The third and fourth images (FIGS. 5 and 6) were both taken at 970 nm under parallel polarization and cross-polarization conditions, respectively.

Figure 7:
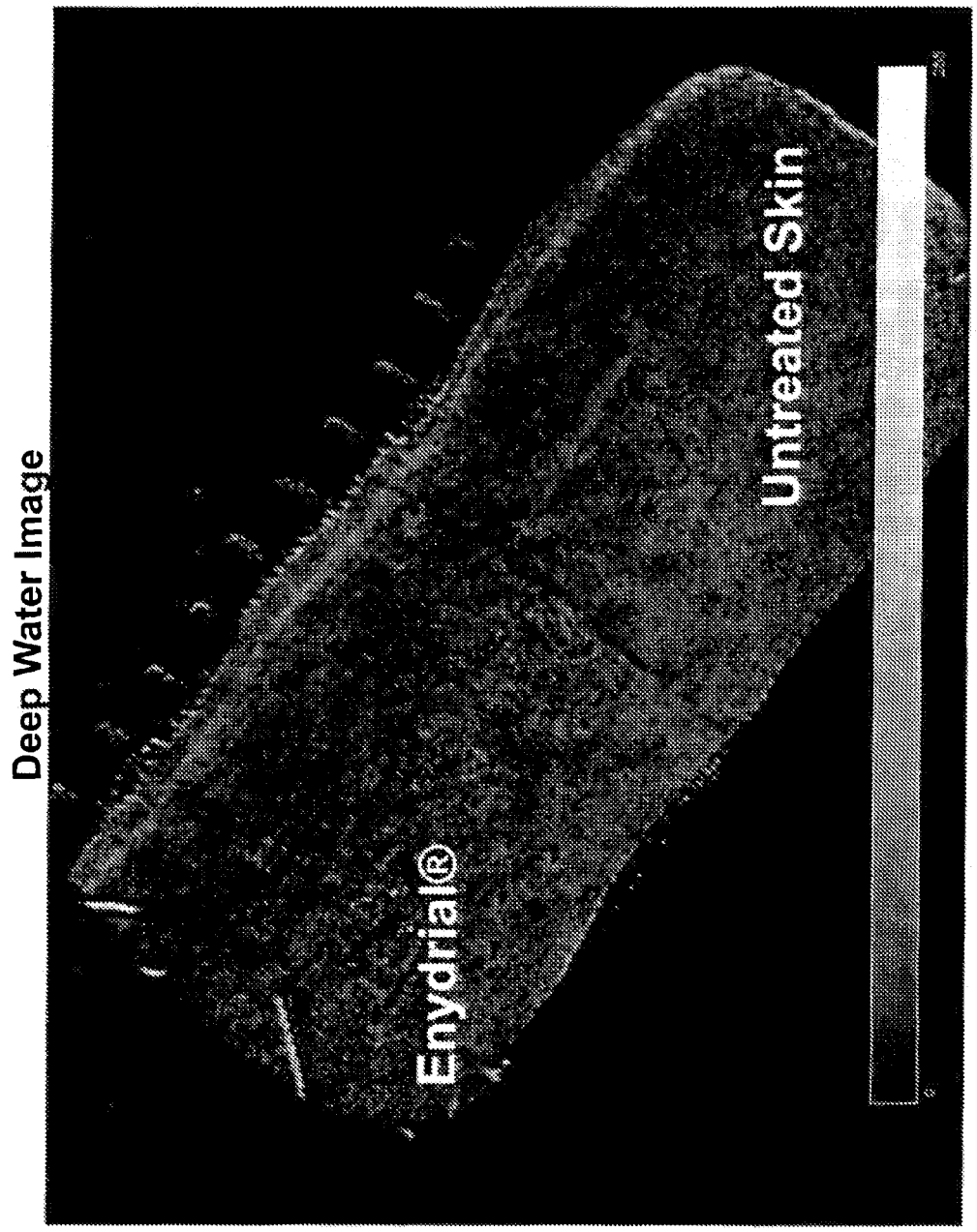
FIG. 7 shows the deep water map generated using the images shown in FIGS. 4 and 6.

The images were then processed using the following equations to obtain the deep and surface water content:

Deep (Viable Epidermis and Dermis) Water Map (FIG. 7):

$$-\log\left(\frac{\text{reflectance at } 970\lambda_{XP}}{\text{reflectance at } 800\lambda_{XP}}\right)$$

Figure 8:
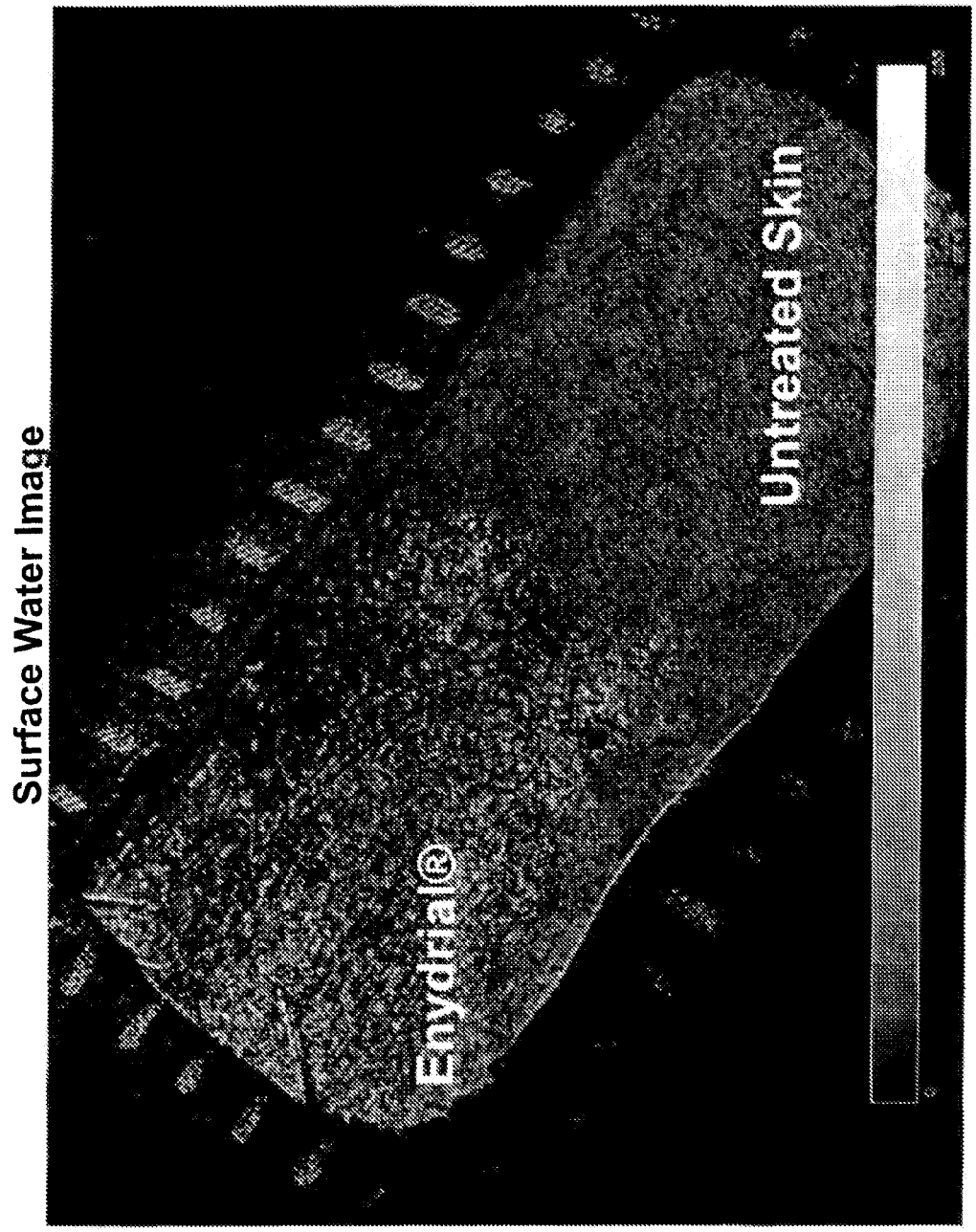
FIG. 8 shows the surface water map generated using the images shown in FIGS. 3-6

Surface (Stratum Corneum) Water Map (FIG. 8):

$$-\log\left(\frac{\text{reflectance at } 970\lambda_{PP} - \alpha \text{ reflectance at } 970\lambda_{XP}}{\text{reflectance at } 800\lambda_{PP} - \alpha \text{ reflectance at } 800\lambda_{XP}}\right)$$

where $\alpha=0.30$.

The increased hydration from the moisturizing cream is visible in the surface water map.

What is claimed is:

1. A method for measuring skin hydration comprising:
   a) acquiring a first digital image of skin under parallel polarization conditions filtered at a first wavelength $\lambda_{1PP}$ of from about 700 to about 900 nm;
   b) acquiring a second digital image of skin under orthogonal polarization conditions filtered at the first wavelength $\lambda_{1XP}$ of from about 700 to about 900 nm;
   c) acquiring a third digital image of skin under parallel polarization conditions filtered at a second wavelength $\lambda_{2PP}$ of from about 900 to about 1000 nm;
   d) acquiring a fourth digital image of skin under orthogonal polarization conditions filtered at the second wavelength $\lambda_{2XP}$ of from about 900 to about 1000 nm;
   e) using a processing means, generating reflectance values for each of the four digital images; and
   f) using a processing means, applying the reflectance values to the following Equation I:

$$-\log\left(\frac{(\text{reflectance at } \lambda_{2PP} - \alpha \text{ reflectance at } \lambda_{2XP})}{(\text{reflectance at } \lambda_{1PP} - \alpha \text{ reflectance at } \lambda_{1XP})}\right)$$

wherein $\alpha$ is a parameter used to adjust to account for the amount of diffused reflected light in said parallel polarized images and is between about 0.2 and about 0.4, such that said processing means generates a fifth digital image of the skin using the output of Equation I.

2. The method of claim 1, wherein the fifth digital image is generated before treatment.

3. The method of claim 1, wherein the fifth digital image is generated after treatment.

4. The method of claim 1, wherein the first wavelength is about 800 nm.

5. The method of claim 1, wherein the second wavelength is about 970 nm.

6. The method of claim 1, wherein $\alpha$ is about 0.3.

* * * * *